United States Patent [19]

Stuber et al.

[11] Patent Number: 4,570,010

[45] Date of Patent: Feb. 11, 1986

[54] PRODUCT

[75] Inventors: Fred A. Stuber; George H. Temme, both of North Haven, Conn.

[73] Assignee: The Upjohn Company, Midland, Mich.

[21] Appl. No.: 478,128

[22] Filed: Mar. 23, 1983

[51] Int. Cl.$^4$ .............................. C07F 7/08; C07F 7/10
[52] U.S. Cl. ................................... 556/475; 556/417; 556/419; 556/420; 556/422; 264/400; 264/DIG. 83; 264/51; 521/111
[58] Field of Search ............... 556/420, 425, 417, 419, 556/422

[56] References Cited

U.S. PATENT DOCUMENTS

| | | | |
|---|---|---|---|
| 2,814,572 | 11/1957 | Frye | 556/425 X |
| 3,389,160 | 6/1968 | Reid | 556/425 X |
| 3,420,782 | 1/1969 | Dahm et al. | 556/425 X |
| 3,509,196 | 4/1970 | Plueddemann et al. | 556/425 |
| 3,993,606 | 11/1976 | vonBonin et al. | 260/2.5 AH |
| 4,033,912 | 7/1977 | Kleimann et al. | 260/2.5 AH |
| 4,036,868 | 7/1977 | Atherton | 556/425 X |
| 4,038,221 | 7/1977 | Roster et al. | 260/2.5 AH |
| 4,052,495 | 10/1977 | Uhlmann et al. | 264/216 |
| 4,220,727 | 9/1980 | Godlewski | 521/110 |
| 4,350,777 | 9/1982 | Henrichs et al. | 521/110 |
| 4,430,335 | 2/1984 | Chu et al. | 556/425 X |
| 4,477,366 | 10/1984 | Robertson | 252/182 |

FOREIGN PATENT DOCUMENTS

| | | | |
|---|---|---|---|
| 2363452 | 6/1975 | Fed. Rep. of Germany | 556/425 |
| 3012126 | 10/1981 | Fed. Rep. of Germany | 556/425 |
| 1494930 | 12/1977 | United Kingdom | 556/425 |

Primary Examiner—Paul F. Shaver
Attorney, Agent, or Firm—James S. Rose

[57] ABSTRACT

Disclosed is an improved process for the production of organic polyisocyanate-based molded polymers prepared from at least one organic polyisocyanate and at least one polyol wherein there is employed an internal mold release agent comprising an amino-polysiloxane having at least one group of the formula RNH-alkylene—O— bonded to a silicon atom of a polysiloxane, wherein R is selected from the group consisting of hydrogen, lower-alkyl, cycloalkyl, and ECHR"CHR'— wherein E is an electron withdrawing group and R' and R" are independently selected from the group consisting of hydrogen and methyl.

The molding process can be repeated many times before the mold surfaces must be cleaned or treated with release agent. The ease of release of the molded polyurethanes makes the process particularly suitable for RIM production methods.

4 Claims, No Drawings

PRODUCT

BACKGROUND OF THE INVENTION

1. Field of the Invention

This invention relates to an improved process for molding polyisocyanate-based polymers and is more particularly concerned with improving the mold release properties of said polymers through the use of internal release agents.

2. Description of the Prior Art

The molding of polyisocyanate-based articles both cellular and non-cellular, in a variety of shapes and using an assortment of polymer compositions and mold materials, is well known in the art. To prevent the molded pieces from sticking to the mold surfaces, mold release agents are generally employed. These agents can be in the form of external or internal release agents. The external agents, substances such as waxes, soaps, oils, and the like, are applied at regular intervals to the mold surface. The molding operation must be stopped frequently to allow for cleaning and reapplication of fresh release agent. The internal type of agents are much the preferred release agents because they invariably provide for multiple releases before the mold must be closed down for cleaning. This, in turn, leads to the production of a greater number of parts in a given time period for a mold using internal as opposed to external release agents.

Generally speaking, the internal release agents are derived from polysiloxanes which can be divided into two broad classes; (1) release agents that have terminal silicon to carbon bonds and are thereby stable to hydrolysis (non-hydrolyzable); and (2) release agents that have terminal silicon to oxygen to carbon bonds and are thereby susceptible to hydrolysis (hydrolyzable). In most cases the non-hydrolyzable release agents are preferred because of their greater stability, particularly in the basic reactive polyurethane forming environment.

Typical examples of the use of the non-hydrolyzable type of release agents can be found in German patent application 23 634 52 which discloses the esterification products derived from mono- or polycarboxylic acids (8 to 40 carbons) with polysiloxanes having hydroxymethyl groups attached directly to silicon atoms; U.S. Pat. No. 3,993,606 which discloses the salts of fatty acids with certain amino-polysiloxanes wherein the amino groups are connected to the silicon through a methylene radical; U.S. Pat. No. 4,220,727 which discloses, inter alia, certain organofunctional carboxyalkylsiloxanes; U.S. Pat. No. 4,350,777 which discloses various hydroxyl, primary amino, and secondary amino terminated polysiloxanes; U.S. Pat. No. 4,033,912 which discloses the reaction products of mono- or polyisocyanates with polysiloxanes having hydroxymethyl, or certain secondary aminomethyl, groups attached to the silicon atoms; and German patent application No. 30 121 26 which discloses hydroxyl terminated reaction products derived from the reaction of an excess of at least difunctional alcohols or aminoalcohols with isocyanate terminated prepolymers which latter are derived from the reaction of an excess of a polyisocyanate with a hydroxy, amino, or mercapto terminated polysiloxane of the non-hydrolyzable type.

Typical examples of the use of the hydrolyzable type of polysiloxanes can be found in U.S. Pat. No. 4,038,221 which discloses tertiary aminoalkoxy polysiloxanes not as internal mold release agents per se but as a replacement for various emulsifiers, stabilizers, and activators, in the preparation of cellular polyurethanes; U.S. Pat. No. 4,052,495 which discloses a class of hydroxyl terminated polyoxyalkyleneoxy siloxanes; and British Pat. No. 1,494,930 which discloses salts of amino group containing polysiloxanes with a fatty acid having more than 7 carbon atoms wherein the amino group containing polysiloxane substrates include primary, secondary, and tertiary amino terminated alkylene (non-hydrolyzable) and alkyleneoxy (hydrolyzable) siloxanes.

Those release agents which carry organofunctional end groups such as hydroxyl and amino have generally been employed in some prereacted form rather than directly in a one-shot process. This is done to avoid stability problems in the event the polysiloxane release agent is of the hydrolyzable type, and because hydroxyl terminated polysiloxanes are notoriously incompatible and unreactive with polyurethane forming ingredients. For example, U.S. Pat. Nos. 4,033,912 and 4,350,777, cited supra, specifically in the former and preferably in the latter, call for the use of the release agent in prepolymer form to be added to the urethane forming ingredients in the mold. In U.S. Pat. No. 4,052,495 the reactive hydroxyalkyleneoxysiloxanes are added to an uncured non-cellular urethane prior to the curing of the latter in a mold. For the sluggishly reactive types of internal release agents, such prereactions described above are particularly necessary where a rapid molding procedure is called for, as, for example, in RIM preparations.

We have now discovered an improved process for the production of molded polyisocyanate based polymers wherein the use of a particular class of primary or secondary amine terminated hydrolyzable type polysiloxane imparts outstanding release properties to the molded articles. In fact, the exceptionally large number of mold releases which can be obtained before the mold must be refurbished makes the use of the present process particularly appropriate in RIM applications.

Additionally, the molds containing the polymers prepared in accordance with the present invention can be opened much more easily than those molds containing formulations employing prior art release agents.

In yet another surprising feature, molded polyurethane articles in accordance with the present invention possess a high degree of paintability. The majority of the prior art release agents provide parts which do not have good paintability.

In contrast to the prior art hydroxyl terminated polysiloxane release agents of the type noted above, the present compounds enjoy a wide range of compatibility with the polyurethane forming ingredients. Additionally, they react faster into the polyurethane matrix than the hydroxyl polysiloxanes. These attributes thereby eliminate the prior art necessity of prereacting the agents with either polyisocyanate or polyurethane prepolymer and the polyurethane forming process can be carried out in a one-shot type process if desired. At the same time, the release agents are locked into the formulation and cannot migrate from the molded part at some later time.

Surprisingly, it has been discovered that the primary amino-polysiloxanes used in accordance with the present invention, and, which correspond to those primary aminoalkyleneoxypolysiloxanes employed in the British Pat. No. 1,494,930 in the form of the acid salts, behave quite differently from the reference release agents.

A comparison of the reactivity of polyurethane formulations employing the internal mold release agents in accordance with the present invention as opposed to formulations in accordance with the British reference discloses the much faster reactivities of the former over the latter. In fact, the slowness of the prior art formulations, in some cases, would preclude their use in preparing RIM parts, particularly large RIM parts.

SUMMARY OF THE INVENTION

This invention comprises a process for the production of an organic polyisocyanate based polymer in a closed mold which comprises polymerizing a reaction mixture comprising at least one organic polyisocyanate with at least one organic polyol the improvement which comprises employing in said process an internal release agent comprising an amino-polysiloxane having at least one group of the formula $$RNH-alkylene-O- \qquad (I)$$

bonded to a silicon atom of a polysiloxane wherein R is selected from the group consisting of hydrogen, lower-alkyl, cycloalkyl, and ECHR"CHR'— wherein E is an electron withdrawing group and R' and R" are independently selected from the group consisting of hydrogen and methyl, said amino-polysiloxane being substantially free of any acid salt thereof.

This invention also comprises a novel class of amino-polysiloxanes having the formula $$ECHR"CHR'NH-alkylene-(OSiR_1R_2)_{\overline{m}}O-alkylene-NHCHR'CHR"E \qquad (II)$$

wherein E is an electron withdrawing group and R' and R" are independently selected from the group consisting of hydrogen and methyl, $R_1$ and $R_2$ are independently selected from the group consisting of methyl and phenyl, and m has an average value of from about 3 to about 100.

The term "polysiloxane" has the generally accepted meaning well known to those skilled in the art and means a polymer having a MW from about 250 to about 50,000 and comprised of organosiloxane units having the generalized formula $$R_n'''SiO_{\frac{4-n}{2}} \qquad (III)$$

wherein R''' is selected from the group consisting of lower-alkyl and aryl, and n is an integer from 1 to 3, inclusive. It will be obvious to one skilled in the art that those organosiloxane units having n=3 are representative of polymer chain ending units while those units having n=2 and n=1 are representative of difunctional units and branch units respectively in the polymer chain.

While the polysiloxane should contain at least one group of formula (I), it preferably contains from 2 to 4 such groups.

The term "electron withdrawing group" means a group capable of attracting electrons and is inclusive of —CN, —COOR, —CONH$_2$, —NO$_2$, —SOR, and SO$_2$R wherein R has the definition set forth above except for the exclusion of hydrogen.

The term "alkylene" means straight or branched chain alkylene having from 1 to 8 carbon atoms, inclusive, such as methylene, ethylene, propylene, butylene, pentylene, hexylene, heptylene, octylene, and isomeric forms thereof.

The term "lower-alkyl" means alkyl having from 1 to 8 carbon atoms, inclusive, such as methyl, ethyl, propyl, butyl, pentyl, hexyl, heptyl, octyl, and isomeric forms thereof.

The term "aryl" means the radical obtained by removing one nuclear hydrogen atom from an aromatic hydrocarbon having from 6 to 12 carbon atoms, inclusive, and is inclusive of phenyl, tolyl, xylyl, naphthyl, biphenylyl, and the like.

The term "cycloalkyl" means the radical obtained by removing one hydrogen atom from a ring carbon atom of a cycloaliphatic hydrocarbon having from 3 to 6 carbon atoms, inclusive, and is inclusive of cyclopropyl, cyclobutyl, cyclopentyl, cyclohexyl, methylcyclohexyl, and the like.

DETAILED DESCRIPTION OF THE INVENTION

Various types of polyisocyanate-based polymers can be employed in the process in accordance with the present invention. Typical, but not limiting thereof, are the molded polyurethanes, polyurethane-polyureas, polyisocyanurates, polyurethane-polyisocyanurates, polyamide-polyurethanes, etc. For illustrative and detailed teaching in regard to the preparation of molded polyurethanes including reactants and various molding procedures, reference is made to the prior art cited supra, and particularly, U.S. Pat. Nos. 3,993,606; 4,033,912; 4,038,221; 4,052,495; 4,220,727 and 4,350,777 whose disclosures relative thereto are hereby incorporated herein by reference. Also incorporated herein by reference for typical molded polyisocyanurate preparations are U.S. Pat. Nos. 3,896,052; 3,899,443 and 3,903,018.

In carrying out the preparation of the molded polyurethanes in accordance with the present invention any of the molds and materials employed conventionally in the construction of said molds can be employed. Advantageously, the molds are fabricated from metals such as cast aluminum, steel, steel alloys, stainless steel, chrome-alloys, electroform nickel/copper, and the like.

The preferred type of polyisocyanate based polymers for use in the process in accordance with the present invention are the polyurethane based polymers including those polymers which additionally include polyurea linkages and polyisocyanurate linkages in conjunction with the polyurethane. A preferred means for molding the polyurethanes in accordance with the present invention is by the RIM method. For specific teaching directed to the preparation of polyurethanes by the RIM method see U.S. Pat. Nos. 4,218,543; 4,296,212; 4,321,333 and 4,342,841 whose respective disclosures are herein incorporated by reference.

The novelty in the present invention resides in the use, as an internal release agent in the preparation of the above molded polymers, of an amino-polysiloxane containing at least one of the aminoalkyleneoxy groups (I) defined above and preferably 2 to 4 of such groups. It will be appreciated by those skilled in the art that included within such polysiloxanes are oligomeric siloxanes, polymeric siloxanes, including linear, branched, and cross-linked polysiloxanes, and even cyclic siloxanes, and mixtures thereof, provided they fall within the MW range set forth above and contain at least one of the aminoalkyleneoxy groups (I). For a discussion and description of oligomeric, polymeric, and cyclic siloxanes see Chemistry and Technology of Silicones by W. Noll, 1968, Academic Press, New York, N.Y.

A preferred class of amino-polysiloxanes for use as internal mold release agents in accordance with the present invention is the linear polysiloxanes having the formula

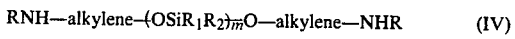

RNH—alkylene—(OSiR$_1$R$_2$)$_{\overline{m}}$O—alkylene—NHR  (IV)

wherein R and alkylene are defined as above, R$_1$ and R$_2$ are independently selected from the group consisting of methyl and phenyl, and m has an average value of from about 3 to about 100.

Those polysiloxanes (IV) wherein R is ECHR"CHR'— represent a novel class of polysiloxanes (II) defined above.

Preferred within the above class of linear polysiloxanes (IV) are those wherein alkylene is ethylene, R$_1$ and R$_2$ are both methyl, m has an average value of about 10 to about 75 and R is hydrogen or ECHR"CHR'— wherein E, R", and R' are defined as above.

The release agents which are used in accordance with the present invention can be added to the polyurethane forming ingredients in any convenient manner. Generally speaking, they can be premixed with any other component of the polyurethane forming ingredients prior to reaction. However, in view of their reactive nature (i.e. the primary or secondary amine functionality), it is preferable that they not be premixed with the polyisocyanate. Alternatively, the release agents can be added in a separate stream to the reaction environment rather than being preblended with another reactant.

The actual amount of release agent to be used will vary according to the particular polyurethane formulation and release agent being employed, and, more particularly, the mold configuration. However, it is used in only minor amounts and those amounts are easily determined by one skilled in the art using trial and error experiments. The term minor amount means an amount sufficient to provide multiple mold releases before the mold requires any cleaning or other surface treatment including the use of a mold release agent on the mold surface.

Generally speaking, the amino-polysiloxane release agent is employed within the range of from about 0.25 percent to about 10 percent by weight based on the total formulation weight, preferably from about 0.5 to about 8 percent, and, most preferably, from about 1 to about 5 percent by weight.

Illustrative, but not limiting, of the linear aminopolysiloxanes, and with the understanding that overall MW will fall within the range set forth above, are α,ω-bis(2-aminoethoxy)-polydimethylsiloxane, α,ω-bis(3-aminopropoxy)-polydimethylsiloxane, α,ω-bis(4-aminobutoxy)-polydimethylsiloxane, α,ω-bis(5-aminopentoxy)-polydimethylsiloxane, α,ω-bis(6-aminohexoxy)-polydimethylsiloxane, α,ω-bis(7-aminoheptoxy)-polydimethylsiloxane, αω-bis(8-aminooctoxy)-polydimethylsiloxane, α,ω-bis(2-amino-2-ethyl-ethoxy)-polydimethylsiloxane, α,ω-bis(4-amino-3-methyl-butoxy)-polydimethylsiloxane, α,ω-bis(2-aminoethoxy)-polydiethylsiloxane, α,ω-bis(2-aminoethoxy)-polydiphenylsiloxane, α,ω-bis(2-aminoethoxy)-polymethylpropylsiloxane, α,ω-bis(2-aminoethoxy)-polymethylphenylsiloxane, α,ω-bis(2-aminoethoxy)-polymethyl(3-cyanopropyl)siloxane, α,ω-bis(2-aminoethoxy)-polymethyl(2-trifluoromethylethyl)polysiloxane, α,ω-bis(N-methyl-2-aminoethoxy)-polydimethylsiloxane, α,ω-bis(N-ethyl-2-aminoethoxy)-polydimethylsiloxane, α,ω-bis(N-propyl-2-aminoethoxy)-polydimethylsiloxane, α,ω-bis(N-butyl-2-aminoethoxy)-polydimethylsiloxane, α,ω-bis(N-pentyl-2-aminoethoxy)-polydimethylsiloxane, α,ω-bis(N-hexyl-2-aminoethoxy)-polydimethylsiloxane, α,ω-bis(N-heptyl-2-aminoethoxy)-polydimethylsiloxane, α,ω-bis(N-octyl-2-aminoethoxy)-polydimethylsiloxane, α,ω-bis(N-isopropyl-2-aminoethoxy)-polydimethylsiloxane, α,ω-bis(N-isobutyl-2-aminoethoxy)-polydimethylsiloxane, α,ω-bis[N-(2-cyanoethyl)-2-aminoethoxy]-polydimethylsiloxane, α,ω-bis[N-(2-cyanoethyl)-3-aminopropoxy]-polydimethylsiloxane, α,ω-bis[N-(2-cyanoethyl)-4-aminobutoxy]-polydimethylsiloxane, α,ω-bis[N-(2-cyanoethyl)-5-aminopentoxy]-polydimethylsiloxane, α,ω-bis[N-(2-cyanoethyl)-6-aminohexoxy]-polydimethylsiloxane, α,ω-bis[N-(2-cyanoethyl)-7-aminoheptoxy]-polydimethylsiloxane, α,ω-bis[N-(2-cyanoethyl)-8-aminooctoxy] polydimethylsiloxane, α,ω-bis[N-(2-cyanopropyl)-2-aminoethoxy]-polydimethylsiloxane, α,ωbis[N-(2-carbomethoxyethyl)-2-aminoethoxy]-polydimethylsiloxane, α,ω-bis[N-(2-carbomethoxypropyl)-2-aminoethoxy]-polydimethylsiloxane, α,ω-bis[N-(2-formamidoethyl)-2-aminoethoxy]-polydimethylsiloxane, α,ω-bis(N-cyclopropyl-2-aminoethoxy)-polydimethylsiloxane, α,ω-bis(N-cyclobutyl-2-aminoethoxy)-polydimethylsiloxane, α,ωbis(N-cyclopentyl-2-aminoethoxy)-polydimethylsiloxane, α,ω-bis(N-cyclohexyl-2-aminoethoxy)-polydimethylsiloxane, and α,ω-bis[N-(4-methylcyclohexyl)-2-aminoethoxy]-polydimethylsiloxane.

Preferred amongst the illustrative species set forth above are those amino-polysiloxanes having the polydimethylsiloxane backbone and having as terminal groups either the aminoethoxy groups or those novel polysiloxanes (II) having the 2-cyanoalkylamino-, the 2-carbomethoxyalkylamino-, and the 2-formamidoethylamino-groups.

The known aminoalkyleneoxy-polysiloxanes to be used in accordance with the present invention are readily obtained by a variety of preparative methods which are exemplified in the following schematic equation.

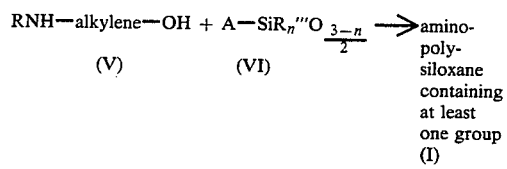

RNH—alkylene—OH + A—SiR$_n$'''O$_{\frac{3-n}{2}}$ ⟶ amino-
    (V)        (VI)                   polysiloxane containing at least one group (I)

Aminoalcohols (V) wherein R and alkylene are as defined above are reacted with polysiloxanes (III) containing at least one organosiloxane unit (VI) wherein A can represent acetoxy, halogen, or hydroxyl, and n is 1 or 2 to form the corresponding polysiloxane containing at least one group (I). The polysiloxane containing at least one of the units (VI) is representative of the oligomeric and polymeric siloxanes including linear, branched, and cross-linked polysiloxanes discussed above. Preferably the polysiloxane (III) contains from 2 to 4 of the units (VI).

In the method where A represents acetoxy in the starting polysiloxane, the acetoxy group is replaced by a trans-esterification reaction in accordance with the method described in detail in U.S. Pat. No. 3,338,859 whose disclosure is incorporated herein by reference.

Alternatively, where A is halogen, particularly chlorine, it is displaced by the aminoalcohol (V) in accordance with the method described in U.S. Pat. No. 4,038,221 whose disclosure is incorporated by reference herein.

In a preferred method, A is hydroxyl so the silanol containing polysiloxane is simply heated together with the appropriate compound (V) to eliminate water and form the corresponding aminoalkyleneoxypolysiloxane in accordance with the method disclosed in "Product Information Bulletin F-212", SWS Silicone Corp., Adrian, Mich.

The novel aminopolysiloxanes (II) are easily prepared in accordance with the following schematic equation.

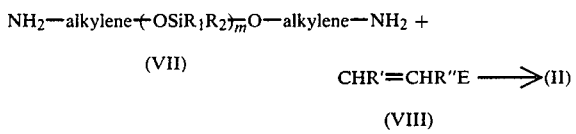

The aminoalkyleneoxypolysiloxanes (VII) are obtained by any one of the methods described above wherein R in starting compound (V) is hydrogen. (VII) is then alkylated with at least a two molar proportion of an ethylenic compound (VIII) wherein E, R' and R" are defined as above to yield the novel compounds (II). Such alkylation reactions and the methods entailed thereby are well known to those skilled in the art. When E is a cyano group, the reaction is the well known cyanoethylation reaction, and, generally speaking, is carried out in accordance with the teaching set forth in Organic Reactions Vol. V, p 79, 1949, John Wiley and Sons, Inc., New York.

When the electron withdrawing group E is other than cyano then the reaction is commonly known as a Michael type reaction (see ibid Vol. 10, p 179 for methods of carrying out this type of reaction). As stated previously the term "electron withdrawing group" is used herein in the sense well known in the art to denote a group which causes polarization of the $\alpha,\beta$-ethylenic compound (VIII) so as to facilitate the addition of an anionic species at the terminal methylene group.

Illustrative of the compounds (VIII) are acrylonitrile, α-methylacrylonitrile, crotononitrile, and the like; methyl acrylate, ethyl acrylate, propyl acrylate, butyl acrylate, pentyl acrylate, hexyl acrylate, heptyl acrylate, octyl acrylate, methyl methacrylate, and the like alkyl acrylates and methacrylates; acrylamide, α-methylacrylamide, and the like; nitroethylene, α-methylnitroethylene, and the like; methylvinyl sulfone, ethylvinyl sulfone, butylvinyl sulfone, methylvinyl sulfoxide, ethylvinyl sulfoxide, and the like.

A preferred group of compounds (VIII) comprise the acrylonitrile, alkyl acrylate and alkyl methacrylate compounds set forth above.

The products (II) obtained by the above procedures are easily obtained in a purified state simply by distilling the reaction mixtures, preferably under reduced pressure, so as to remove any volatiles, and, in particular, any excess or unreacted compound (VIII).

The molded polyurethanes prepared in accordance with the present invention can be prepared using any of the polyols having two or more hydroxyl groups known in the prior art. Primarily, the choice of polyol functionality and molecular weight will depend on the specific polymer properties required and the type of polyol employed. Advantageously, polyols having a primary hydroxyl functionality of from about 2 to about 4 and a MW of from about 1500 to about 12,000 can be used in the present polymers.

Generally speaking, the preferred functionality will be from about 2 to about 3 with a preferred MW from about 2000 to about 8000.

While the polyols mentioned hereinabove refer to primary hydroxyls this is not to imply that minor amounts of secondary hydroxyl groups cannot be present, either in the same molecule with the primary groups, or in a separate polyol component.

Any of the polyols disclosed in the patents cited supra and falling within the definition above can be employed in the present process.

A preferred group of polyols comprises the propyleneoxy-polyethyleneoxy capped diols and triols obtained by the alkoxylation of water, ammonia, ethylene glycol, propylene glycol, trimethylolpropane, aniline, ethanolamine, and the like; the polyester diols obtained from the reaction of dibasic carboxylic acids such as succinic, adipic, suberic, azelaic, phthalic, isophthalic, and the like with alkylene glycols, and oxyalkylene glycols to form the corresponding polyalkylene, and polyoxyalkylene ester diols or copolymers thereof; and the vinyl-resin reinforced propyleneoxy-ethyleneoxy capped diols and triols, particularly those polyethers reinforced with polyacrylonitrile.

The organic polyisocyanates to be used in accordance with the present invention can be any of the organic di- or higher functionality polyisocyanates known to those skilled in the polyurethane art and may be aliphatic, cycloaliphatic, aromatic, or heterocyclic polyisocyanates such as those described by Siefken in Justus Liebigs Annalen der Chemie, 562, pages 75 to 136.

The preferred class of polyisocyanates is the aromatic polyisocyanates and the preferred isocyanate functionality is about 2. Most preferably, the polyisocyanates are aromatic isocyanates that are essentially diisocyanates which are in the liquid state at room temperature (circa 20° C.).

Any of the organic polyisocyanates disclosed in the patents cited supra and falling within the definition above can be employed in the present process.

A preferred group of organic polyisocyanates includes the various types of liquified 4,4'-methylenebis(phenyl isocyanate) such as those disclosed in U.S. Pat. Nos. 3,384,653; 3,394,164 and 3,394,165 wherein storage stable liquid methylenebis(phenyl isocyanates) are obtained by reacting said methylenebis(phenyl isocyanates), including the 4,4'-isomer, the 2,4'-isomer, and mixtures of said 4,4'- and 2,4'-isomers in varying proportions with minor amounts of either a trihydrocarbyl phosphate, or dipropylene glycol, or N,N-di(2-hydroxypropyl)aniline respectively; the liquid diisocyanates comprising the carbodiimide-containing methylenebis(phenyl isocyanates) having an isocyanate equivalent weight of from about 130 to about 180 in accordance with U.S. Pat. No. 3,384,653.

Also included within the scope of the organic polyisocyanates to be used in accordance with the present invention are the isocyanate-terminated polyurethane prepolymers prepared from any of the typical polyisocyanates and polyols disclosed above in any proportions wherein the equivalents of the starting polyisocyanate are in excess over the polyol equivalents. Particularly preferred in this regard are the prepolymers prepared from 4,4'-methylenebis(phenyl isocyanate) and polyoxyethylenepolyoxypropylene diols or triols, polytetramethylene glycols, or polyester diols and triols.

Particularly useful, and to be included in the compounds having two or more isocyanate reactive hydrogen atoms in accordance with the present invention, are the extenders well known to those skilled in the polyurethane art. Particularly preferred are the difunctional extenders. Typical extender classes are the low molecular weight diols, diamines, aminoalcohols and the like having a MW falling within a range from about 60 to about 400, and mixtures of any of the above types of extenders.

Illustrative of the extenders, but not limiting, are ethylene glycol, 1,3-propylene glycol, 1,2-propylene glycol, 1,4-butanediol, 1,2-hexanediol, neopentyl glycol, and the like; diethylene glycol, dipropylene glycol, and the like; and dihydroxyalkylated aromatic compounds such as the bis(2-hydroxyethyl)ethers of hydroquinone and resorcinol; p-xylene-$\alpha,\alpha'$-diol; the bis(2-hydroxyethyl)ether of p-xylene-$\alpha,\alpha'$-diol; m-xylene-$\alpha,\alpha'$-diol and the bis(2-hydroxyethyl)ether thereof, and the like; and 1,3-diethyl-2,4-diaminobenzene, 2,4-diaminomesitylene, 1-methyl-3,5-diethyl-2,4-diaminobenzene, 1-methyl-3,5-diethyl-2,6-diaminobenzene, 3,3',5,5'-tetraisopropyl-4,4'-diaminodiphenylmethane; and the like. Typical of mixed extenders which can be used in the present invention are those disclosed in U.S. Pat. No. 4,296,212 cited supra.

The relative equivalent proportions of said polyol component to said extender can vary over a wide range depending on specific molecular weights and the properties desired in the polyurethane polymer. Generally speaking, the equivalent proportions of the former to the latter is within the range of about 1:4 to about 1:40, and preferably about 1:10 to about 1:35; most preferably about 1:10 to about 1:20.

The proportions of polyisocyanate to the total active hydrogen equivalents, comprised of the polyol and the extender, are such that the ratio of isocyanate equivalents to the total active hydrogen equivalents falls within a range of from about 0.95 to 1.5, preferably about 1.00 to about 1.2, and most preferably 1.00 to 1.10.

In this connection, it should be noted that the amino polysiloxanes in accordance with the present invention carry active hydrogens. For the most part, the equivalents of these silicones are small and they can be disregarded when calculating the isocyanate to active hydrogen equivalents. However, in the event that the equivalents involved are sufficiently high so as not to be disregarded then the particular value can be included within the above ranges.

In an optional, and preferred embodiment in accordance with the present invention, a urethane forming catalyst is present in said polyurethane forming ingredients.

Any of the catalysts conventionally employed in the art to catalyze the reaction of an isocyanate with itself and/or with a reactive hydrogen containing compound including those disclosed in the patents cited supra can be employed for this purpose.

The preferred urethane catalysts are the organo metallic compounds and particularly the dialkyl tin salts such as the dibutyltin compounds noted above.

The amount of catalyst employed can vary considerably according to the particular reactants in the polymer forming mixture and the particular catalyst involved. Optimum catalyst concentration is easily determined using trial and error tests by one skilled in the art. Generally speaking, the catalyst or mixture of catalysts will be employed within a range of from about 0.01 percent by weight to about 5.0 percent by weight preferably from about 0.02 to about 3.0 percent, most preferably from about 0.05 percent to about 0.5 percent based on the total weight of isocyanate, polyol, and extender.

Optionally, blowing agents may be employed wherein compact tough skinned surfaces are desired. Any of the blowing agents known to those skilled in the art can be used including water and the fluorocarbon blowing agents. The latter are preferred and generally are halogenated aliphatic hydrocarbons which can be also substituted by chlorine and/or bromine in addition to the fluorine content; see U.S. Pat. No. 3,745,133, column 11, lines 25 to 38 which disclosure relating to fluorocarbon blowing agents is incorporated herein by reference.

Also, inert gases (e.g. nitrogen) may be introduced at the polymer forming stage to provide whatever degree of blowing is desired to produce products ranging from micro-cellular to macro-cellular in nature.

Other optional additives such as dispersing agents, cell stabilizers, surfactants, flame retardants, colorants, and the like can be added to the polyurethane polymers in accordance with the present invention.

The molding process in accordance with the present invention can be repeated in an unexpectedly high number of molding cycles before any mold surface treatment is required and the molds can be opened more easily than prior art molded polyurethanes. Consequently, these advantages speed up a production line, cut down on reject rate, and thereby lead to considerable economic advantage.

Accordingly, the molded polyurethane articles produced in accordance with the present invention are useful, inter alia, for the preparation of solid cast elastomers, solid and microcellular RIM elastomers, and elastoplastics. The molded products find particular utility as auto parts such as car bumpers, body elements, panels, doors, engine hoods, skirts, air scoops, and the like. Further, the thermosetting nature of the present polymers results in their good high temperature performance characteristics which make them suitable for industrial elastomer applications where high temperature resistance is needed such as in paint drying chambers.

The following examples describe the manner and process of making and using the invention and set forth the best mode contemplated by the inventors of carrying out the invention but are not to be construed as limiting.

PREPARATION I $\alpha,\omega$-Bis(2-aminoethoxy)-polydimethylsiloxane

A 100 ml. three-neck flask fitted with a magnetic stirrer, condenser, and regulating thermometer, was charged with 50.36 g. (0.02 mole) (based on suppliers weight percent hydroxyl content of 1.9% and assuming all dihydroxyl species) of a linear $\alpha,\omega$-dihydroxy-polydimethylsiloxane (sample designation F-212 supplied by SWS Silicones, Cleveland, Ohio), 8.22 g. (0.136 mole) of ethanolamine, and 50 ml. of toluene. The averge value for m for the dimethylsiloxy repeat units was determined from the proton nuclear magnetic resonance (NMR) spectrum of the silanol by integration of the silyl methyl groups vs the hydroxyl protons and back calculated from the weight percent hydroxyl functionality of the silanol to provide an average value of $m=30$.

The reaction mixture was stirred and heated at 115° C. and the conversion was followed by NMR analysis of aliquot samples at 1 or 2 hour intervals. The samples were concentrated in vacuo, dissolved in carbon tetrachloride and washed with deuterated water prior to determining the NMR spectrum in deuterated chloroform. Using the same proton integration comparison method described above for each sample spectrum, the conversion was determined. It was assumed that an average m value of 40 was indicative of 100% conversion because under optimum conditions as determined from a series of similar runs, the value of $m=40$ was the lowest number measured. This higher value of 40 compared to the starting value of $m=30$ is probably due to some further polymerization of the starting silanol.

After 4.5 hours at 115° C. NMR analysis showed 51% conversion and after 20 hours a 93% conversion. At this point the toluene was removed by distillation until the reaction pot temperature reached 150° C. and the mixture was cooled. Water of reaction and some of the excess ethanolamine azeotroped over with the toluene. The residue was then heated to a pot temperature of 150° C. under 1 mm of mercury pressure to provide a yellow oil. Thus there was obtained the α,ω-bis(2-aminoethoxy)-polydimethylsiloxane having the formula

NMR analysis of the final product showed an average value of $m=41$ or 97.5% conversion.

PREPARATION II

α,ω-Bis(N-methyl-2-aminoethoxy)-polydimethylsiloxane

A 1 liter three-neck flask fitted with a magnetic stirrer, thermometer, and a reflux condenser over a Dean-Stark trap, was charged with 170 g. (0.1 mole) of a linear α,ω-dihydroxy-polydimethylsiloxane (sample designation PS340 supplied by Petrarch Systems Inc., Santa Barbara, Ca) having $m=24$ determined using the NMR procedure described in the previous preparation, 15.3 g. (0.2 mole) of N-methylethanolamine, and 150 ml. toluene.

The solution was heated under reflux and after 2 hours about 3 ml. of water was collected in the trap. Continued reflux overnight yielded an additional 3 ml. of water in the trap. NMR analysis on the combined water fractions showed (assuming the 6 ml. was approximately 6 g.) 2.8 g. of water and 3.2 g. of methylethanolamine.

An additional 8.8 g of N-methylethanolamine was added to the reaction solution and reflux resumed for 3 hours which produced a 1.0 g. aqueous phase in the trap. The toluene was distilled off until the pot temperature reached 215° C.

The residue was then distilled under vacuum (about 0.5 mm of mercury) to remove excess methylethanolamine and toluene until the pot temperature reached 215° C. leaving a residue of yellow oil. Thus there was obtained the α,ω-bis(N-methyl-2-aminoethoxy)-polydimethylsiloxane having the formula

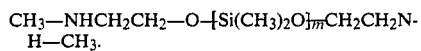

NMR analysis showed an average value of $m=32$ and the yield was 170.5 g. (about 88%).

EXAMPLE 1

A five liter, three-neck flask fitted with a thermometer, a magnetic stirrer, and a distillation head was charged with 1495.2 g. (0.43 mole) of an α,ω-bis(2-aminoethoxy)-polydimethylsiloxane [prepared in accordance with the procedure set forth in Preparation I and having an average value of $m=45$] and 466.2 g. (8.8 mole) of acrylonitrile. The reaction mixture was allowed to stand at room temperature (circa 20° C.) for 24 hours.

At the end of the 24 hour period, the excess acrylonitrile was removed by distillation under 2 to 10 mm of mercury pressure and heated such that the pot temperature remained below 75° C. leaving a residue of a yellow oil. Thus there was obtained the α,ω-bis[N-(2-cyanoethyl)-2-aminoethoxy]-polydimethylsiloxane in accordance with the present invention having the formula

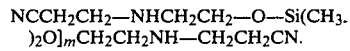

NMR analysis of the product showed a 96% conversion (or average value of $m=48$) and a yield of 1508.2 g. or 98.7%.

EXAMPLE 2

A 2 liter flask fitted with a magnetic stirrer, and thermometer was charged with 517 g. (0.19 mole) of an α,ω-bis(2-aminoethoxy)polydimethylsiloxane prepared in accordance with the procedure set forth in Preparation I and having a value of $m=35$, and 202 g. (2.35 mole) of methyl acrylate. The mixture was allowed to stand 24 hours whereupon an aliquot sample was removed, concentrated, and analyzed by NMR as described above, showing an $m=31$. The reaction solution was stirred for an additional 18 hours. No significant change in the integration of any of the NMR signals could be observed and m was calculated to be 34.

The excess methyl acrylate was removed by distillation at aspirator pressure (about 10 mm of mercury) until the pot temperature reached 160° C. leaving a residue of yellow oil. Thus there was obtained α,ω-bis[N-(2-carbomethoxyethyl)-2-aminoethoxy]-polydimethylsiloxane having the formula

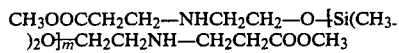

wherein m has an average value of 34.

NMR analysis of the product showed no starting material but the presence of about 5% of end units assumed to be from α,ω-bis[N,N-di(2-carbomethoxyethyl)-2-aminoethoxy]-polydimethylsiloxane having the formula

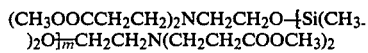

531.4 g. of product was obtained or a yield of 97%.

EXAMPLE 3

The following series (A through D) of molded polyurethane plaques was prepared using a hand-mix technique and the same formulation throughout except for the variation in internal mold release agent employed in each series. Master batches of an A side (isocyanate) and B side (polyol) were prepared and a number of multiple moldings were made from these A and B components for each series.

The isocyanate employed as the A component was a modified liquid methylenebis(phenyl isocyanate) (MDI) obtained by treating an MDI comprised of about 94 percent by weight of the 4,4'-isomer and 6 percent of the 2,4'-isomer in accordance with U.S. Pat. No. 3,384,653 so that about 9.6 percent of the original isocyanate groups were consumed to form carbodiimide. The isocyanate equivalent weight of this liquid product was 143.7 and contained about 0.056 equivalent of carbodiimide.

The B component was prepared by blending together in the following proportional parts by weight: 100 parts of SF 6503 (a 6500 MW polypropyleneoxy-polyethyleneoxy triol, OH E.W.=2100, supplied by Texaco Chemical Co.); 20 parts of ethylene glycol; 0.075 part of dibutyl tin dilaurate; 0.10 part of a surfactant which is a proprietary blend of alkylarylsulfonate and alkoxylated alcohols (supplied by Arjay Inc., Houston, Tex.); and 6.67 parts of the appropriate internal mold release agent set forth below.

The A component in the proportion of 102.2 parts (NCO index=1.02) was mixed with the B component in a quart cup for about 10 secs. using a 2300 RPM drill press motor fitted with a stirring blade. The stirred reaction mass was immediately poured into an 8"×8"×⅛" chrome steel mold heated to 150° F. and held for 2 to 3 minutes in the heated mold. The molded plaques were demolded and observed for the degree of difficulty of demolding and green strength.

The number of moldings for each series of A through D was chosen to be 20 (except in B where not enough mold release agent was available to allow for that many moldings). At the beginning of each 20 sample series the mold was preconditioned by first being cleaned with a mold cleaner (Mold Wiz is a mold cleaner supplied by Axel Corp., Woodside, N.Y.). Then an external mold release (XMR-136 is a mold release was supplied by Chem Trend Co., Howell, Mich.) was applied and the mold surfaces buffed. The application of XMR-136 and buffing was repeated.

Plaque series A and B, are in accordance with the present invention wherein the internal mold release agents employed were α,ω-bis[N-(2-cyanoethyl)-2-aminoethoxy]-polydimethylsiloxane (m=48), and α,ω-bis(N-methyl-2-aminoethoxy)-polydimethylsiloxane (m=32) respectively.

Plaque series C and D are in accordance with the prior art wherein the internal mold release agents employed were α,ω-bis(diethylamino)-polydimethylpolysiloxane (m=47) and ethyl oleate respectively.

In plaque series A twenty molding cycles were carried out with excellent release in all 20 demoldings, plaque green strength was good as well as tensile and elongation properties. Series B yielded 10 demoldings with the release rating being slightly behind A in terms of ease of release.

In regard to plaque series C even though reactivity was good and demolding was easy the samples cracked. In the case of D while the samples did not crack, the release rating went from excellent to very poor before the 20 cycles were completed.

TABLE I

| Plaque Series | A | B | C | D |
|---|---|---|---|---|
| Number of Releases | 20 | 10[1] | 20 | 20 |
| Release Rating[2] | 0 | 1 | 0 | 0 to 5 |
| Green Strength[3] | good | good | cracked | good |
| Elongation (%) | 138 | 88 | 103 | 127 |
| Tensile Str. (psi) | 2342 | 2100 | 2050 | 1983 |

[1]The quantitity of mold release agent available was sufficient only for 10 complete molding cycles. There was nothing to indicate that the mold in B needed any conditioning so that the molding cycles could have continued if the material had been available.
[2]Release Rating is a rating on a scale of 0 to 5 of the ease which a plaque is removed from the mold with 0 being the easiest up to 5 which signifies the most difficult removal. Where a rating is listed 0 to a particular number this signifies that the demolding increases in difficulty as the number of cycles increases up to 20.
[3]Green Strength is an art recognized test in which the freshly demolded piece while still warm and without curing is bent manually to about a 90 degree bend to form a crease. Visual observation is made of the extent of surface cracking, if any, on the sample.

EXAMPLE 4

The following series (E through I) of molded polyurethane plaques were prepared using a pilot plant scale reaction injection molding machine and the same A and B components as set forth in Example 3 with the exceptions noted below.

One tank of the RIM machine was charged with the modified liquid MDI and employed in the proportion of about 107.2 parts so as to be at an NCO index of 1.07. The second tank was charged with the B component which differed from B in Example 3 in having the dibutyl tin dilaurate in the proportions of 0.15 part, and 3.5 parts of the respective internal mold release agents (1.5 percent by weight of the total formulation) set forth below except for plaque series H which contained no internal mold release and series I which contained 7 parts of its release agent (3 percent by weight of the total formulation). The A and B component temperatures were 100 to 120 and 115 to 130 respectively. Metering pumps from each tank were used to deliver the ingredients into the impingement mixing head of the RIM machine. After mixing, the reaction mixture was directed into a metal mold measuring 12"×8"×⅛" which was at a mold temperature of 150° F. and which had been pretreated as described in Example 3.

Upon demold the mold was observed for degree of difficulty in opening (manually), whether the plaque released easily from the mold surfaces, and whether any deposition of material had occurred, as well as the number of releases. Following this, the samples were cured at 250° F. for 1 hour before being subjected to the test procedures set forth in Table II. Each molding series was continued until some indication was observed that the mold needed to be cleaned and fresh external release applied to the surfaces.

Plaque series E through G, inclusive, are in accordance with the present invention whereas series H and I are not.

In series E the internal release was α,ω-bis(2-aminoethoxy)-polydimethylsiloxane (m=45) and 73 plaques were molded before mold cleaning was indicated. A slight film deposition was noted on the mold beginning at the 35th molding. However, this did not interfere with the demolding operation. In a second series E in which the same mold release was used in double the proportions (7 parts) 75 parts were made with no deposition whatsoever.

In series F the internal release agent was α,ω-bis[N-(2cyanoethyl)-2-aminoethoxy]-polydimethylsiloxane (m=45) and at the 1.5 percent level it allowed 40 parts to be molded. A few of the initial moldings left a slight deposit on the mold. However, the deposited material was removed in subsequent moldings.

In series G the internal release agent was α,ω-bis[N-(2-carbomethoxyethyl)-2-aminoethoxy]-polydimethylsiloxane (m=34) and at the 1.5 percent level 40 parts were made with no deposition of any material.

In series H no internal release was used and by the third molding the plaque had to be pried from the upper mold face. By the seventh molding the series was stopped due to the difficulty in opening the mold.

In series I the internal release agent was ethyl oleate at the 3 percent by weight level. Adhesion of the parts to the mold was noted after 26 moldings and a thin film beginning to deposit on mold surfaces after 30 parts.

The three series E, F, and G displayed excellent demolding characteristics whereas H with only a few moldings and I with its deposition of material on the mold surface both had poor demolding characteristics.

The good physical properties for series E through G samples as set forth in Table II show that the use of the internal release agents have no adverse affects on the other polymer physical properties and in some instances result in property improvements.

TABLE II

| Plaque Series | E | F | G | H | I |
| --- | --- | --- | --- | --- | --- |
| Number of Releases | 73 | 40 | 40 | 3[1] | 32[2] |
| Physical Properties: | | | | | |
| Density g/cc. | 0.852 | 1.022 | 1.028 | 0.996 | 0.994 |
| Hardness Shore D | 55 | 55 | 55 | 55 | 51 |
| Elongation (%) | 170 | 190 | 240 | 210 | 210 |
| Tensile str. (psi) | 2300 | 2940 | 3290 | 3140 | 2640 |
| Tensile Set (%) | 40 | — | 60 | 60 | — |
| Die C Tear (pli) | 500 | 730 | 600 | 680 | 580 |
| Split Tear (pli) | 120 | — | — | 160 | — |
| Flex Modulus (psi) | 20,610 | 34,570 | — | 30,440 | 23,120 |
| Heat Sag[3], inches 250° F./hr. | 1.72 | — | — | 1.86 | — |

[1]After only 3 demoldings the plaque had to be pried from the upper mold surface. The molding cycle was continued and after 7 plaques the mold was very difficult to pry open so molding cycle was stopped.
[2]Slight adhesion of plaque to the mold was noted after 26 parts had been demolded. After 30 parts a very thin film was deposited on the upper mold surface. RIM machine malfunction necessitated cessation of molding cycle at 32.
[3]Heat sag is determined in accordance with Test CTZ 006AA of the Chevrolet Div. of General Motors Corp., Flint, Mich. It is the amount, in inches, that a 1 inch wide its own weight when held at one end in a horizontal position under the specified conditions of time and temperature.

EXAMPLE 5

This example sets forth a comparison of the reaction gel times for two hand-mix sample polyurethane formulations 1 and 3 in accordance with the present invention with two hand-mix sample polyurethane formulations 2 and 4 respectively in accordance with the prior art (British Pat. No. 1494930).

Hand-mix sample 1 was prepared by mixing together in a paper cup using a wooden tongue depressor 101.2 parts of the liquid MDI described in Example 3 with a preblended B component. The B component was comprised of the following ingredients: 100 parts of SF 6503; 20 parts of ethylene glycol; 0.8 part of 1,4-diazabicyclo(2.2.2)octane (DABCO); 0.1 part of dibutyl tin dilaurate; and 6 parts of α,ω-bis(2-aminoethoxy)-polydimethylsiloxane (m=35). The components were stirred until the mixture stiffened suddenly preventing further stirring. This time was recorded in seconds as the gel time.

Sample 2 was prepared similarly to sample 1 using the same ingredients in the same proportions except that instead of 6 parts of the α,ω-bis(2-aminoethoxy)-polydimethylsiloxane there was used 6 parts of an oleic acid addition salt prepared from the same α,ω-bis(2-aminoethoxy)-polydimethylsiloxane (m=35) above and oleic acid on a 1:1 equivalent basis. It will be noted that sample 2 formulation is in accordance with British Pat. No. 1 494 930 and the catalyst ingredients and proportions are particularly in accordance with Example 17 of that reference.

Sample 3 and comparison sample 4 were prepared similarly to samples 1 and 2 using the same procedure and ingredients with the same diaminopolysiloxane internal release agent as in sample 1 being used in sample 3 and the same oleic acid salt thereof as in sample 2 being used in sample 4. The difference in this set of samples was the employment of just the single catalyst species of 0.075 part of dibutyl tin dilaurate (6 drops) which places the catalysis of samples 3 and 4 closer to the formulations set forth in Example 3 above.

The gel times for the respective samples were as follows

| | Gel Time (secs.) |
| --- | --- |
| Sample 1 | 15 |
| Sample 2 | 40 |
| Sample 3 | 19 |
| Sample 4 | 106 |

It should be noted that in order for polyurethane formulations to be compatible with RIM processing techniques they should have hand-mix gel times that are fast. In this connection, using the urethane test formulation of this example, gel times greater than 20 to 25 seconds would be considered too long. Formulations having gel times exceeding this upper limit must be additionally catalyzed, if, indeed, this can be accomplished without disturbing polymer properties. Clearly, samples 2 and 4 have gel times which exceed this upper limit.

We claim:

1. An amino-polysiloxane having the formula

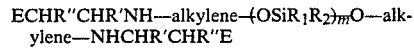

$$ECHR''CHR'NH\text{—alkylene—}(OSiR_1R_2)_mO\text{—alkylene—}NHCHR'CHR''E$$

wherein $R_1$ and $R_2$ are independently selected from the group consisting of methyl and phenyl, E is an electron withdrawing group and R' and R'' are independently selected from the group consisting of hydrogen and methyl, and m has an average value of from about 3 to about 100.

2. An amino-polysiloxane according to claim 1 wherein alkylene is ethylene and $R_1$ and $R_2$ are both methyl, and m has an average value of from about 10 to about 75.

3. An amino-polysiloxane according to claim 2 wherein the group ECHR''CHR'— is 2-cyanoethyl and m has an average value from about 40 to about 50.

4. An amino-polysiloxane according to claim 2 wherein the group ECHR''CHR'— is 2-carbomethoxyethyl and m has an average value from about 30 to about 40.

* * * * *